United States Patent

Smit

Patent Number: 6,096,047
Date of Patent: Aug. 1, 2000

[54] GYNECOLOGICAL CYLINDERS WHICH TREAT DISEASES

[76] Inventor: Julie Ann Smit, 1045 Hinman Ave., Evanston, Ill. 60202

[21] Appl. No.: 09/146,740

[22] Filed: Sep. 3, 1998

Related U.S. Application Data

[60] Provisional application No. 06/060,030, Sep. 25, 1997.

[51] Int. Cl.[7] .................................................. A61B 17/42
[52] U.S. Cl. .................. 606/119; 606/191; 600/208; 600/235; 600/573; 600/551
[58] Field of Search .................................. 604/104, 285; 606/119, 191, 193; 600/208, 211, 235, 551, 576, 581, 573

[56] References Cited

U.S. PATENT DOCUMENTS

| | | | |
|---|---|---|---|
| 471,647 | 3/1892 | Magoris | 604/104 |
| 3,192,928 | 7/1965 | Horton . | |

OTHER PUBLICATIONS

Horton, Robert R., M.D., "Treatment of Vaginitis, An Anatomic and Physiologic Approach", Postgraduate Medicine, vol. 32, No. 3, pp. 222–228, Sep. 1962.

*Primary Examiner*—Jeffrey A. Smith

[57] ABSTRACT

The entrance to and walls of a woman's vaginal tract are normally in a constricted state. The fact that air cannot readily enter the vagina and circulate within is at the root of or complicates the treatment of many, common female diseases. For example, many of the disease organisms which attack the vagina are anaerobic which means they cannot thrive or survive in oxygen. Studies show that most die almost at once if exposed to air. Accordingly, it is an object of this invention to insert a highly porous, cylindrical device into the vagina in order to expand the vaginal opening and canal within. After air is allowed to freely enter the vaginal canal, anaerobic organisms are rapidly destroyed.

10 Claims, 3 Drawing Sheets

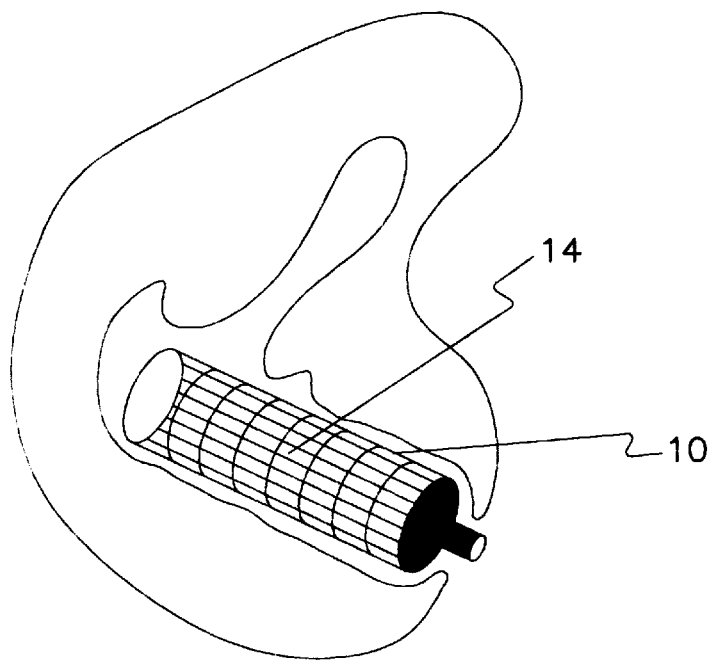
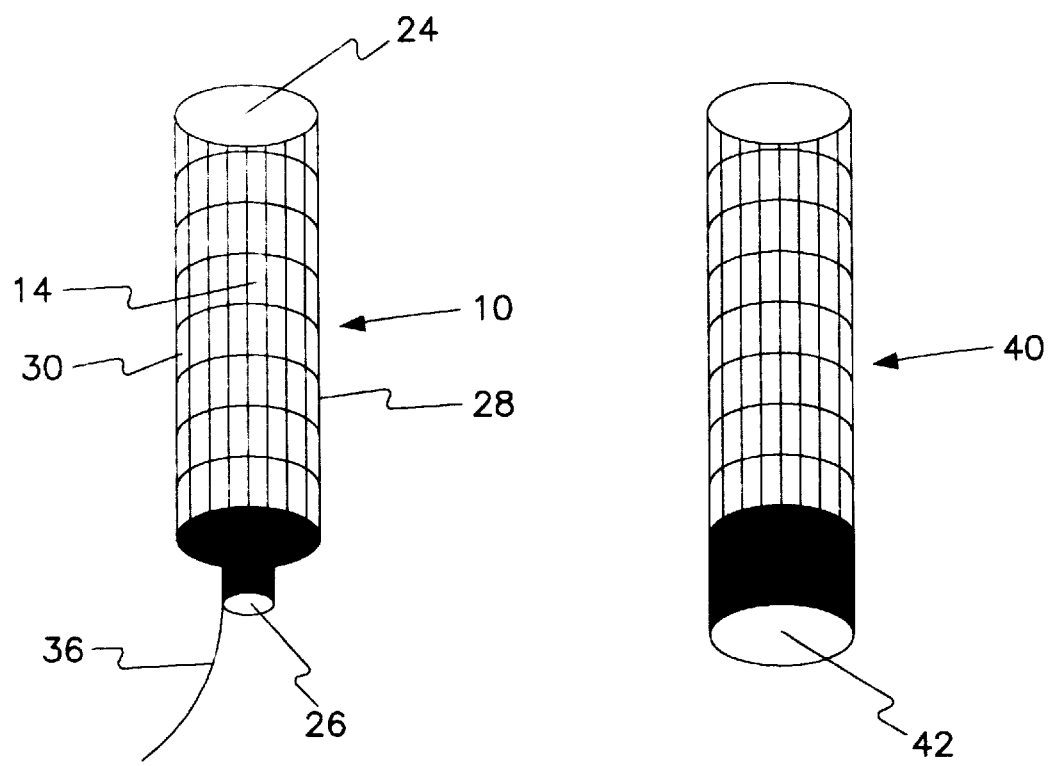

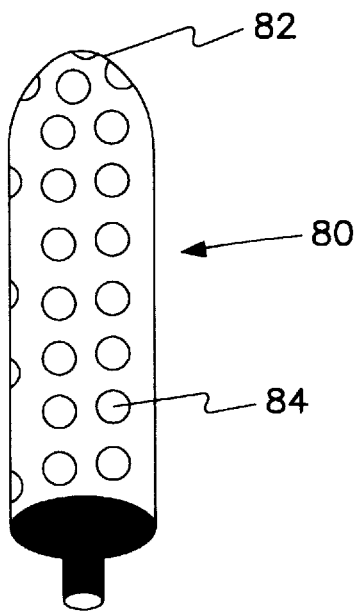
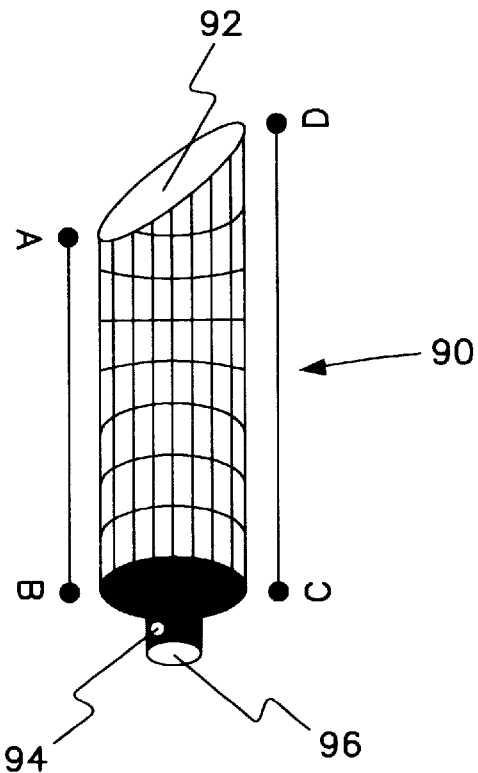
FIG. 6    FIG. 7
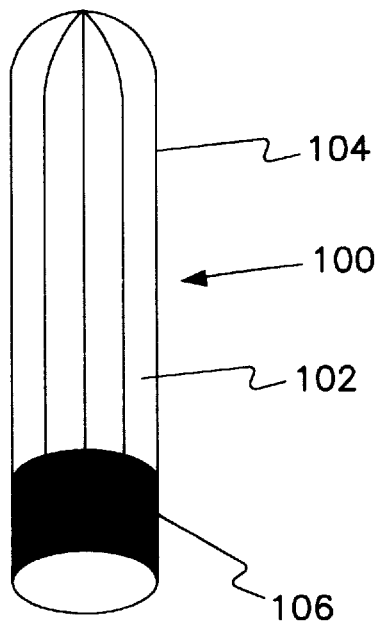
FIG. 8

GYNECOLOGICAL CYLINDERS WHICH TREAT DISEASES

This is a formal Application for Patent of my provisional application, Ser. No. 60/060,030 dated Sep. 25, 1997, entitled: Gynecological Cylinders which Treat Diseases.

This invention is generally a self-treatment in feminine hygiene products and more particularly a porous, hollow instrument which will oxygenate the vagina and cervix to kill anaerobic organisms which cause diseases.

Numerous infections of the female vaginal tract stem from or are exacerbated by a lack of air within the vagina. This is because the entrance to and walls of the vagina are normally constricted and do not readily allow air to enter and circulate.

In general, the organisms causing many vaginal diseases can live only in the warm, moist, anaerobic-type conditions found inside the birth canal. These organisms die quite rapidly if exposed to air or are allowed to become dry or cool.

Studies show, yeast infections can usually be prevented simply by permitting more oxygen to enter the vagina. Additionally, the organisms causing most sexually transmitted diseases die almost at once, after exposure to air; *THE FAMILY BOOK ABOUT SEXUALITY*, revised edition, by Mary S. Calderone, M.D., and Eric W. Johnson, page 186, paragraph three.

Accordingly, sexual diseases such as cylamydia, gonorrhea, syphilis, aids, trichomonas vaginalis, gardnerella vaginalis and others are killed almost immediately when exposed to air.

It is an object of this invention to open and expand the vaginal walls in order to kill anaerobic organisms which cause diseases.

It is a further object of this invention to destroy these anaerobic organisms while still contained within the vagina.

Yet another object of this invention is to stretch and expand the vaginal walls to allow more of the vaginal and cervical surface areas to be oxygenated or irrigated.

Still another object is to capture and remove vaginal and cervical secretions to aid a woman in an early detection of diseases or as a guide to when ovulation is about to occur.

Yet another object is to use the inventive device as an applicator of medicines and substances into the vagina for treatment, thereof.

All these objects and others will become more apparent from a look at the attached drawings, wherein:

FIG. 1 shows a highly, porous cylindrical instrument implanted within the vaginal tract;

FIG. 2 shows one embodiment for the porous vaginal cylinder in which the external open end is of a narrow diameter so as not to stimulate nerve endings;

FIG. 3 shows an alternative embodiment where the external open end is wider in diameter to allow for a greater flow of oxygen or irrigation into the vaginal canal;

FIG. 6 shows an alternate embodiment for a tapered design;

FIG. 7 shows still another embodiment for the vaginal cylinder designed to better reach the top of the vagina; and FIG. 8 shows a whisk-type instrument which contains more open areas.

Figure 4:
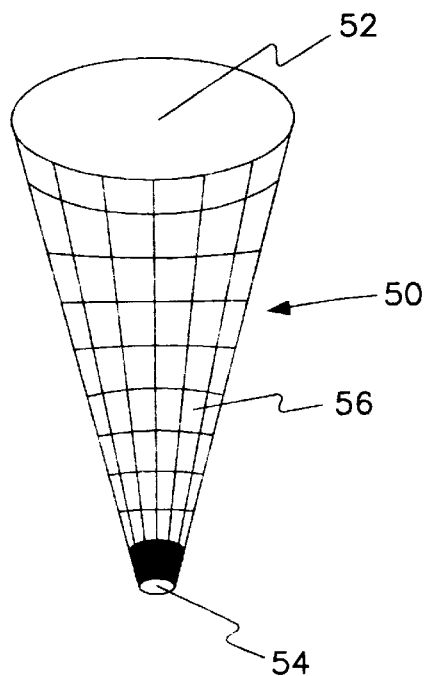
FIG. 4 shows another embodiment, whereby, the vaginal cylinder is a funnel to stretch the walls outwardly.

In greater detail, the vaginal tract is approximately 2½ inches long as measured along its anterior or front wall and approximately 3½ inches long as measured along its posterior or back wall. In its normal state, the walls of the vagina are constricted, basically closing the vaginal tract. The normally constricted state of the vagina does not readily allow air to freely circulate, which is at the root of or complicates the treatment of many female diseases.

Many of the disease organisms which attack the vagina are anaerobic which means they cannot thrive or survive in oxygen. Studies show that most die almost immediately if exposed to air.

Additionally, many of the disease organisms which attack the vagina, are usually contained within the vagina. This is achieved via the cervix which is in a constricted state except during menstruation when it opens.

Additionally, the cervix secretes a thick mucous which acts as a bacteriostatic barrier in order to prevent disease organisms from entering the uterus.

However, some diseases such as clyamydia, gonorrhea, syphilis, and aids will usually penetrate the barrier of cervical mucous, within a short time, if left untreated. Therefore, if the inventive instrument were conceivably used to destroy the more invasive venereal diseases, treatment would have to commence immediately.

For the most part, however, the inventive cylinder is intended as a self-treatment for the anaerobic diseases more readily contained within the vagina, such as trichomonas vaginalis, garnerella vaginalis, yeast infections and the like.

In operation, the inventive cylinder would be inserted into the vaginal tract to open and expand the walls, thereof. After a period of oxygenation, anaerobic organisms which cause diseases would be killed. It is a further purpose of this invention to kill these anaerobic organisms while they are still contained within the vaginal tract.

In greater detail, FIG. 1 shows the vaginal cylinder 10 implanted within the vagina of a woman. Vaginal cylinder 10 contains a hollow vestibule 14 which communicates with open areas in the cylinder for allowing a free circulation of air into the vagina and cervix.

FIG. 2 schematically shows the vaginal cylinder 10 which can be made of any suitable medical-grade, plastic, rubber or the like. Preferably, the vaginal cylinder 10 is approximately 3 inches long, however, it can be any desired length. Vaginal cylinder 10 contains an internal open end 24 which rests in the cervical area and an external open end 26 which extends slightly from the vagina. The walls 28 of vaginal cylinder 10 contain a multiplicity of space openings 30 which communicate with the external open end 26 via hollow vestibule 14. The size of the space openings 30 should be at least 2 millimeters in diameter to prevent them from becoming clogged too readily with vaginal secretions.

External open end 26 may be formed from a solid, smooth section of tube so as not to create any friction against the nerve endings in that area.

In more detail, the vaginal tract has very few nerve endings except for near the entrance, thereto. Therefore, when the vaginal cylinder 10 is in place, very little, if anything, is felt (similar to a tampon or diaphragm). External open end 26 may be approximately ⅛ inch in diameter so as not to activate much sensation, even at the entrance to the vagina.

The internal open end 24 and body of vaginal cylinder 10 may be approximately ⅝ inch in diameter to open and expand the vaginal walls. However, it should be clear that any size and shape vaginal cylinder may be used depending upon how much of the vaginal surface needs to be stretched and treated. Furthermore, a healthy woman may opt to wear a very narrow cylinder ⅛ inch in diameter by 3 inches long, for 1–2 hours, once a month, to simply keep anaerobic organisms in check.

Additionally, a string 36 may be supplied to external open end 26 to aid in removal.

In operation, the vaginal cylinder 10 is inserted into the vaginal tract to open and expand the walls. Oxygen readily enters through external open end 26 and flows through hollow vestibule 14 and out through space openings 30 and internal open end 24. After a period of oxygenation, anaerobic organisms which cause diseases are killed.

FIG. 3 shows an alternate embodiment for the inventive instrument. Here the vaginal cylinder 40 has an external open end 42 which is not narrowed to allow more oxygen or irrigation into the vagina. This embodiment would be desirable during a sitz bath as more saline or vinegar would bathe the vaginal walls and cervix.

For this treatment, a woman would fill a bathtub with warm water up to hip deep and add ½ cup salt or vinegar or a combination of both. The woman would insert the vaginal cylinder 40 to open and expand the vagina and let the warm saline bath cleanse the vaginal walls and cervix. Everyone knows the wonderful benefits of a salt water gargle for a throat infection. The warm salt water properties are equally beneficial for vaginal infections.

In fact, according to Gideon G. Panter, M.D. in *THE WOMAN'S ENCYCLOPEDIA OF HEALTH AND NATURAL HEALING*, by Emrika Padus, senior editor of "Prevention" Magazine, page 503, paragraph 4; "Soaking in this salty bath and inserting your finger into the vagina to enable salty water to enter make an excellent first line of attack against most vaginal infections. Nine out of 10 times a few of these baths at bedtime will clear up the infection and save a trip to the doctor's office."

The highly, porous vaginal cylinder will allow the vaginal walls to be opened and bathed much more effectively than a finger, which blocks. Therefore, the sitz bath will be an even more effective treatment when used in conjunction with the inventive cylinder.

FIG. 4 shows the inventive device formed into a funnel 50. Internal open end 52 stretches the walls of the vagina and cervix, to a greater extent, for oxygenating or irrigating a greater surface area. In use, oxygen would enter through external open end 54 and communicate with the vaginal walls in areas of space openings 56 and internal open end 52.

Figure 4B:
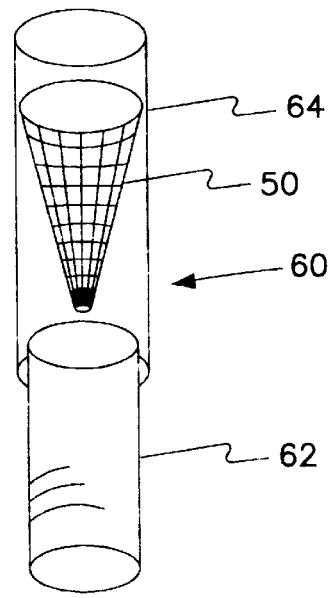
FIG. 4B shows a means for compressing the funnel for insertion into the body.

FIG. 4B shows funnel 50 compressed inside applicator 60 (similar in design to a tampon applicator), for easier insertion into the body. Applicator 60 is comprised of a longer, narrower tube 62 which slides into a shorter, wider tube 64. Funnel 50 is compressed inside the wider tube 64.

In operation, wider tube 64 of applicator 60 is inserted into the vagina. The longer, narrower tube 62 extends from the body. When the longer, narrower tube 62 is pushed upward into the wider tube 64, the funnel 50 is forced out and into the vagina. Once funnel 50 is outside applicator 60, it opens of its own resilience and expands the vaginal walls. Applicator 60 is then removed from the body.

Figure 5:
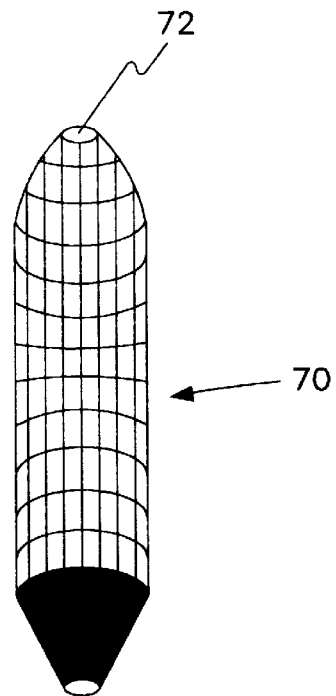
FIG. 5 shows another embodiment for the vaginal cylinder in which the internal open end is tapered for easier insertion into the body.

FIG. 5 shows a different embodiment for the inventive instrument. Here the vaginal cylinder 70 comprises a tapered, internal open end 72 which is easily inserted into the body.

FIG. 6 shows another means for easy insertion. Here vaginal cylinder 80 has a tapered internal end 82 which has multiple space openings 84 to oxygenate the vagina. Additionally, the tapered internal end 82 has no rim to catch or interfere with insertion.

FIG. 7 shows the vaginal cylinder 90 in which the internal open end is a diagonal-cut opening 92 to better fit the top of the vagina.

As previously stated, the front wall of the vaginal tract is approximately 2½ inches long and the back wall is approximately 3½ inches long. Accordingly, vaginal cylinder 90 would include these proportions. Vaginal cylinder 90 as measured along line A–B could be 2½ inches long and as measured along line C–D could be 3½ inches long.

A color-coded dot 94 could be placed on the external open end 96 as an aid in positioning.

FIG. 8 shows a final inventive instrument for oxygenating the vaginal canal. Here the vaginal instrument is a whisk-type device 100 which has large open areas 102 to oxygenate or irrigate the vagina and cervix. The framing bands 104 are rigid enough so as not collapse under pressure from the vaginal walls. Framing bands 104 are incorporated into external open end 106.

In operation, all embodiments of the inventive instrument function similarly. A hollow, porous or open-area device is inserted into the vagina to expand the walls thereof. Oxygen readily enters through an external open end and communicates with the vaginal and cervical walls killing anaerobic organisms, which cause diseases. Additionally, the inventive instrument may be used to irrigate the vaginal and cervical areas.

Further uses for the inventive instrument would be as an applicator of medications and substances into the vagina. For example, medicine or a substance would be spread onto the vaginal cylinder and inserted to both medicate and oxygenate the vaginal tract at the same time.

Additionally, the vaginal cylinder could be used to capture and remove cervical mucous as an aid to when ovulation is about to occur. For example, the mucous of an ovulating woman is of a thinner, more elastic consistency. By viewing such, a woman would know it is the right time to conceive a baby. (In operation, vaginal secretions will collect within the space openings when they are approximately 2 millimeters in diameter.)

Also, possible diseases could be spotted between trips to the gynecologist. For example, if the vaginal cylinder brings out yellow, green, grey, or frothy mucous or blood-tinged mucous or cottage-cheese consistency discharge; clogged within the space openings; (symptoms of various common, female diseases), a woman would know to get a checkup.

Also, female fertility problems are often associated with too much mucous being secreted by the cervix. When this happens, the cervical mucous acts as a barrier which the sperm cannot penetrate, therefore, conception cannot occur. In operation, prior to trying to conceive, the vaginal cylinder would be inserted into the vagina to collect and dry up the cervical secretions, whereby, later the sperm will have an easier access through the cervical canal.

Someone skilled in the art may see various changes which could be made in the inventive instrument. For example, the parts of some embodiments may be exchanged with parts from others. Additionally all sizes and lengths may vary and different types of space openings or open areas could be used. Also, the cylinder could be round, square, oval, etc. as all would basically oxygenate the same. Also, the device could be elongated and inserted into the uterus; thereby, oxygenating or irrigating the vagina, cervix, and uterus. This procedure, of course, would be done under a doctor's care.

Therefore, the appended claims are to be construed broadly enough to cover all equivalent structures falling within the scope and spirit of this invention.

I claim:

1. An instrument for insertion into a gynecological tract to aid a woman in the self-treatment procedure of destroying common, disease organisms located within her gynecological tract, wherein said instrument contains a section of tube tube means comprising for extending beyond the gynecological tract far enough for allowing air or fluid to freely enter into said section of tube, whereby, the air or fluid may be used to treat the gynecological tract and at least a frame means which is connected to said section of tube which holds open the walls of the gynecological tract, said section of tube through which air or fluid enter consisting of a non-irritating contour, said section of tube extending beyond the gynecological tract far enough to allow a free flow of air or fluid into said section of tube and said section of tube continuing into the gynecological tract for the distance necessary in order to bypass the concentrated nerve ending area at the entrance to the gynecological tract from any means other than said section of tube, whereby, a woman will not feel discomfort when the sensitive nerve ending area at the entrance to the gynecological tract is opened and made to bear upon said section of tube because it consists of a non-irritating contour, the end of said instrument which enters the gynecological tract first during insertion containing a tapered end to streamline insertion into the gynecological tract, whereby, this safety feature prevents the gynecological tract from being scratched by said instrument during insertion, and air or fluid entering into an externally located opening on said section of tube, air or fluid flowing through said section of tube and then into said frame means, air or fluid then flowing out openings in said frame means which communicate with the internal walls of the gynecolgcial tract, whereby disease causing organisms within the gynecological tract may be destroyed by a woman in the privacy of her own home.

2. The instrument of claim 1 wherein said instrument comprises an elongated tube with a multiplicity of space-openings.

3. The instrument of claim 2 wherein said space-openings are of a size to capture gynecological secretions within.

4. The instrument of claim 1 wherein said section of tube contains a narrower, diameter so as not to needlessly activate nerve endings.

5. The instrument of claim 1 wherein said section of tube comprises a smooth contour so as not to needlessly activate nerve endings.

6. The instrument of claim 1 wherein said frame means is formed into a funnel to open and expand the walls of the gynecological tract.

7. The instrument of claim 6 whereby said funnel is compressed within an applicator for insertion into the body.

8. The instrument of claim 1 wherein the end of said frame means is diagonal to better fit the top of the vagina.

9. The instrument of claim 1 wherein said instrument oxygenates the vaginal tract in order to kill anaerobic organisms which cause diseases.

10. The instrument of claim 1, wherein said instrument is formed of a medical-grade material.

* * * * *

UNITED STATES PATENT AND TRADEMARK OFFICE
CERTIFICATE OF CORRECTION

PATENT NO. : 6,096,047
DATED : August 1, 2000
INVENTOR(S) : Julie A. Smit

It is certified that error appears in the above-identified patent and that said Letters Patent is hereby corrected as shown below:

Column 5,
Line 5, after "contains" insert -- tube means comprising --.
Line 6, delete -- tube means comprising --.

Signed and Sealed this

Eleventh Day of December, 2001

Attest:

*Nicholas P. Godici*

*Attesting Officer*

NICHOLAS P. GODICI
*Acting Director of the United States Patent and Trademark Office*